(12) United States Patent
Croushorn

(10) Patent No.: US 10,555,741 B1
(45) Date of Patent: *Feb. 11, 2020

(54) DEVICE TO INCREASE INTRA-PELVIC COMPARTMENT PRESSURE FOR THE CONTROLING OF INTERNAL HEMORRHAGE

(71) Applicant: Compression Works, LLC, Birmingham, AL (US)

(72) Inventor: John M. Croushorn, Hoover, AL (US)

(73) Assignee: Compression Works, LLC, Birmingham, AL (US)

( * ) Notice: Subject to any disclaimer, the term of this patent is extended or adjusted under 35 U.S.C. 154(b) by 150 days.

This patent is subject to a terminal disclaimer.

(21) Appl. No.: 15/406,694

(22) Filed: Jan. 14, 2017

Related U.S. Application Data

(60) Provisional application No. 62/278,914, filed on Jan. 14, 2016, provisional application No. 62/278,920, filed on Jan. 14, 2016.

(51) Int. Cl.
*A61B 17/12* (2006.01)
*A61B 17/135* (2006.01)

(52) U.S. Cl.
CPC .. *A61B 17/135* (2013.01); *A61B 2017/12004* (2013.01)

(58) Field of Classification Search
CPC . A61B 5/02233; A61B 5/02241; A61B 5/022; A61B 17/12; A61B 17/132; A61B 17/1322; A61B 17/12209; A61B 17/1325; A61B 17/1327; A61B 17/135; A61B 17/1355; A61B 2017/12004; A61F 5/32; A61F 5/34; A61F 5/012; A61F 2013/0028; A61H 9/005
See application file for complete search history.

(56) References Cited

U.S. PATENT DOCUMENTS 5,464,420 A * 11/1995 Hori ................... A61B 17/1325
606/202

* cited by examiner

*Primary Examiner* — Erich G Herbermann
(74) *Attorney, Agent, or Firm* — The Gache Law Firm, P.C.; Russell C. Gache

(57) ABSTRACT

A device to increase intra-pelvic compartment pressure for the controlling of internal hemorrhages is presented. The device controls internal hemorrhaging by supplementing the occlusion effectiveness of a pneumatic tourniquet with a shaped device that increases the overall internal pressure in a human compartment, such as the inguinal area, to assist in the cessation of bleeding in that region. One side of the device includes a flat base that is adapted to be placed against a patient at the targeted body site. The other side has a generally corrugated shape that is sized to receive an inflatable, wedge-shaped bladder from the pneumatic tourniquet. The overall shape of the invention includes a tapered end that corresponds with the inferior angle of the pubic rami and pelvic area generally so that when pressed against the patient by the pneumatic tourniquet bladder a uniform distribution of pressure occurs over the inguinal area.

20 Claims, 5 Drawing Sheets

DEVICE TO INCREASE INTRA-PELVIC COMPARTMENT PRESSURE FOR THE CONTROLING OF INTERNAL HEMORRHAGE

FIELD OF THE INVENTION

The present invention relates generally to hemorrhage devices and in particular devices for increasing human cavity pressures to control bleeding. The invention also relates to devices for facilitating the cessation of bleeding in a female patient post-partum.

BACKGROUND OF THE INVENTION

A good many deaths result each year from blunt trauma injuries, such as resulting from automobile accidents, aircraft crashes, or bad parachute landings. Dealing with these severe blunt trauma injuries in the field is a nightmare for emergency responders, especially when such trauma occurs to the abdomen. Trauma to the abdominal can result in kidney, spleen, or other solid organ hemorrhages, and often leads to death. For example, a significant spleen laceration can kill a patient in 5-10 minutes if that patient does not receive immediate emergency medical surgery. The standard practice for an emergency responder when abdominal trauma is noticed is to transport the patient as quickly as possible to a hospital where tests can be administered to identify severe bleeding and perform emergency surgery to stop the bleeding. However, quite often transport to a hospital is unavailable or a hospital may be so far away that even under the best transportation scenarios the patient may expire in-route. Further, internal abdominal hemorrhages may not even be identifiable to an emergency responder until systemic symptoms in the patient emerge and by then the patient may only have a few minutes to live.

Field appropriate mechanical and pneumatic tourniquets for the abdomen exist and provide some assistance for abdominal trauma. For example, the Same Junctional Tourniquet ("SAM"), the Combat Ready Clamp, or "CRoC" as it is often referred to, which is simply a large mechanical "C" clamp," and a pneumatic tourniquet offered under the tradename "Abdominal Aortic Tourniquet" or "AAT" are all known and utilized for field trauma victims. However, these solutions tend to be designed for known, specifically located traumas and hemorrhages that can be directly observed and monitored. In addition, these solutions are often inadequate to stop bleeding for internal organ lacerations in the abdomen caused by blunt trauma because the exact location and severity of the laceration often cannot easily be ascertained. For example, the "CRoC" will not assist in stopping an internal abdominal hemorrhage unless that hemorrhage is located relatively close to the surface of the body of the patient and its exact location also known so that proper placement of the compressing member in the CRoC may be applied to the bleeding location.

Pneumatic tourniquets are another potential solution. Pneumatic tourniquets use pneumatic pressure and generally are a targeted application of external pressure to an area of the body to stop blood flow in major blood vessels, such as in the abdomen of a patient. The bladders of a pneumatic tourniquet focus pressure energy under field medic expertise and direction to cause an occlusion of a primary internal blood vessel, such as the aorta. However, the effectiveness of a pneumatic tourniquet is dependent somewhat on the ability for a field medic to recognize the source of the internal bleeding and properly position the pneumatic tourniquet on a patient's abdomen, and such focused pressure while providing some benefit may not stop a hemorrhaging organ such as a spleen from bleeding because it is also supplied with blood from ancillary blood vessels. Further, field responders often have no idea whether an inter-abdominal hemorrhage has occurred, and may not recognize that a pneumatic tourniquet can assist in stopping the hemorrhage. Finally, improper placement or operation of the pneumatic tourniquet may render it ineffective or reduce its effectiveness.

Hence, a medical device is needed for emergency responders to utilize to quickly stop internal abdominal hemorrhaging, at least for a time, until a patient may arrive at a proper medical facility for surgical treatment to the injury.

Such a medical device may be best used in association with pneumatic tourniquets such as described in U.S. Pat. Nos. 8,834,517B2 and 9,149,280B2. As disclosed in those patents, the pneumatic tourniquet inventions include structures for applying pressure to the torso or pelvic area of the human body and the present invention is preferably inserted on the inner side of a pneumatic tourniquet and pressure applied with the operation of the pneumatic tourniquet, such as during inflation.

For example, referring to FIG. 6 of U.S. Pat. No. 9,149,280B2 with those noted elements, pneumatic tourniquets include some minimal structures to function, such as a base plate 18, an inflatable bladder 20 depending downward from the base plate, sometimes connected to the base plate through a foam pad 48 to reduce the impact of the plate on the bladder, an air supply line 60 to fill the bladder, a pressure relief valve 62, and an air bulb pump 58. Pneumatic tourniquets also typically include a waist strap 16 that encircles and secures the pneumatic tourniquet to the patient, including a quick connect buckle 68 and a compression latch 30 for compressing and adjusting same. FIG. 6 of U.S. Pat. No. 9,149,280B2, and the disclosure between Col. 5, line 47 through Col. 6, line 50 of U.S. Pat. No. 9,149,280B2, are hereby incorporated by reference. It will be noted that all pneumatic tourniquets include shaped bladders such that the lower edge of the bladder contacting the patient is less wide than the upper portion contacting the base. This tends to form the bladder into generally a "V" shape having the narrow edge at the lower portion of the bladder contacting the patient upon which it is used.

Therefore, a supplemental device used in association with a pneumatic tourniquet will assist in addressing an abdominal hemorrhage in the field and potentially save lives when imperfect knowledge of a patient's actual internal bleeding condition is known or when timely extraction of a hemorrhaging patient to a surgical facility is impossible.

SUMMARY OF THE INVENTION

It is the object of the present invention to control internal hemorrhaging by supplementing the occlusion effectiveness of a pneumatic tourniquet with a shaped device that increases the overall internal pressure in a human cavity, such as the inguinal area, to assist in the cessation of bleeding in that region. The present invention includes two pieces of rigid plastic placed in opposing position to one another and coupled with grommets or heat welding. One side of the device is a flat base that is adapted to be placed against a patient at the targeted body site. The other side has a generally corrugated shape that is sized to receive an inflatable, wedge-shaped bladder from a pneumatic tourniquet. The overall shape of the invention from a plan perspective is rectangular, but the invention has corners cut on one end to form an angle that corresponds with the inferior angle of the pelvis formed by the anatomical structures of the pubic rami. Other features and objects and advantages of the present invention will become apparent from a reading of the following description as well as a study of the appended drawings.

BRIEF DESCRIPTION OF THE DRAWINGS

A compression device incorporating the features of the invention is depicted in the attached drawings which form a portion of the disclosure and wherein.

DESCRIPTION OF THE PREFERRED EMBODIMENTS

Figure 1B:
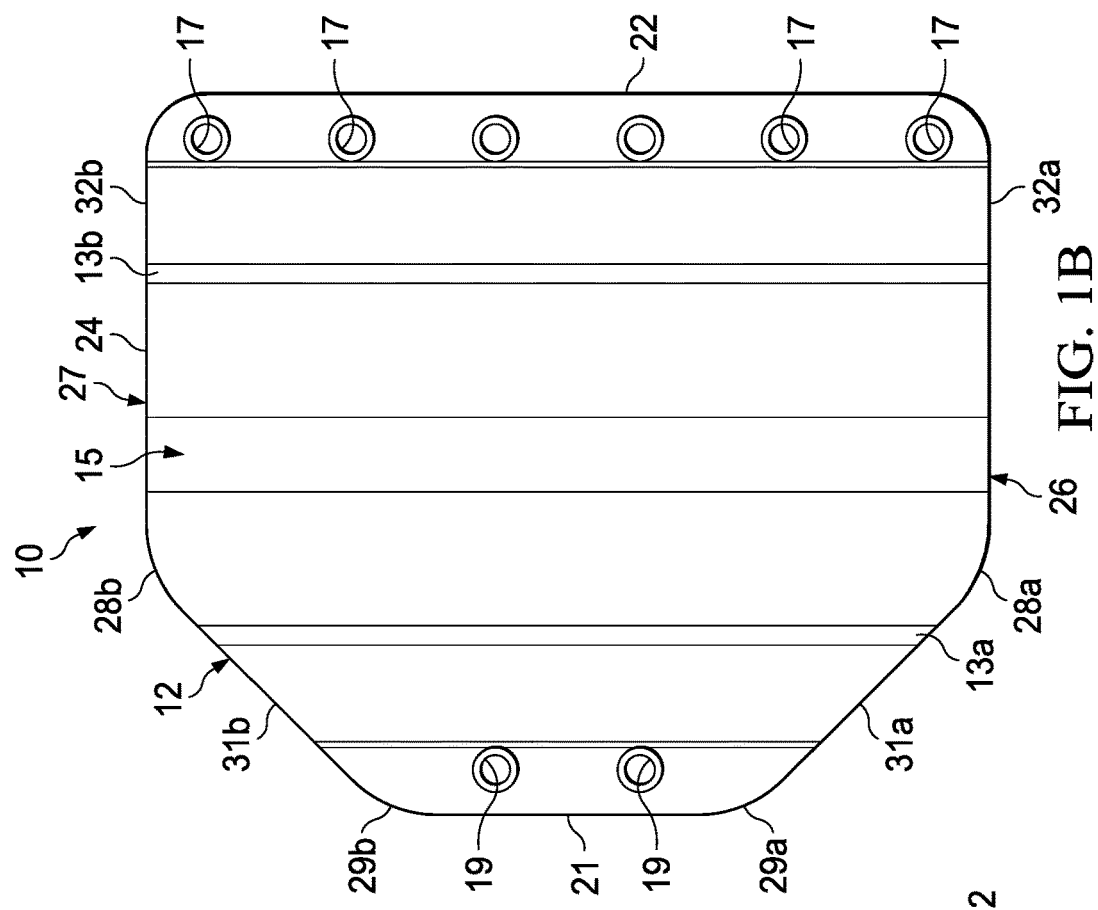
FIG. 1B a plan view of the compression device.
Figure 1A:
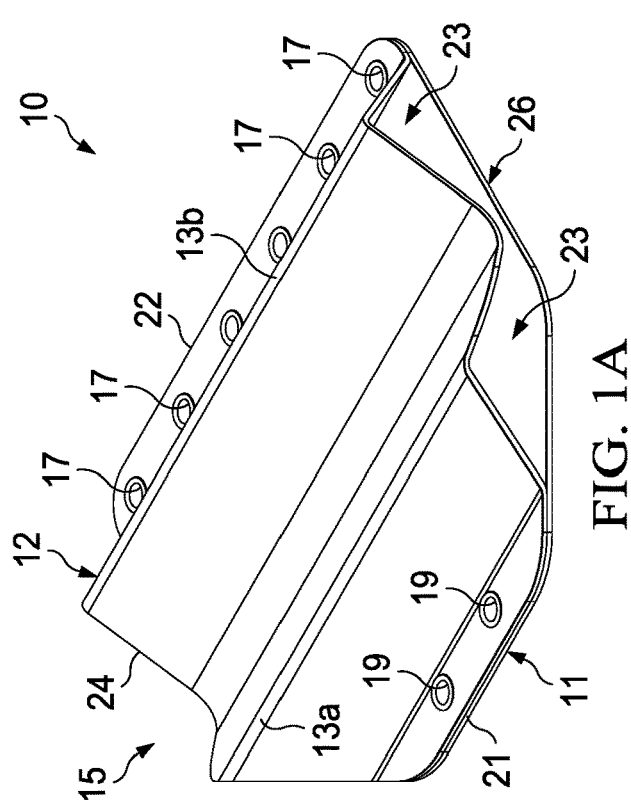
FIG. 1A a top perspective view of the invention compression device.
Figure 1C:
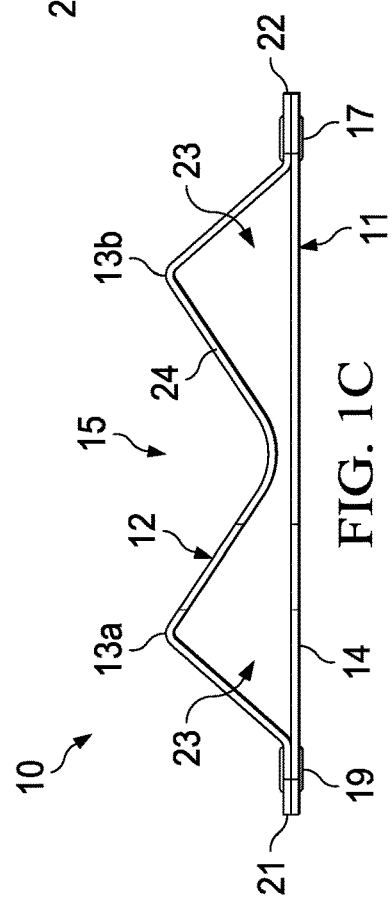
FIG. 1C a side elevational view of the compression device.

Referring to the drawings for a better understanding of the structure and use of the invention, FIGS. 1A-1C provide views of the invention 10 showing the basic elements of the device. Each device 10 includes a lower or base portion 11 that supports an upper corrugated top portion 12. Lower portion 11 is substantially flat and includes a leading edge 21 and a trailing edge 22. Leading and trailing edges are connected along the undersurface 14 of lower portion 11 of the device and along left and right edges 26 and 27. The upper portion 12 and the lower portion 11 are fused at the leading and trailing edges 21, 22 through a series of grommets 17,19 to form a unified body.

As may be seen, upper portion 12 is corrugated such that two upper ridges 13a,b are formed in parallel orientation with respect to leading and trailing edges 21, 22. The two ridges 13a,b form a parallel valley or recess 15 between them that will receive a portion of a pneumatic tourniquet bladder, as will be discussed.

Referring now also to FIGS. 1B and 1C, it may be seen that the device 10 has a generally rectangular in shape with the leading edge 21 having a width substantively less than trailing edge 22. The side edges of upper portion 12 match the side edges of lower portion 11 to form a tapered shape of the device 10 at one end in which approximately a third of the perimeter of the device tapers along the edges 26/27 to the extents of the leading edge 21 as shown. In particular, edges 26/27 include a straight segment edge portion 32a,b and an angled segment portion 31a,b. Tapered edges 31a,b taper from points 28a,b to leading edge points 29a,b forming an angle of approximately 135 degrees at the juncture of segment edges 32a,b and segment edges 31a,b, respectively.

As may be better seen in FIG. 1C, ridges 13a,b form hollow spaces 23 between base portion 11 and top portion 12 having a generally triangular shape.

The combination of straight side edges 32a,b and tapered side edges 31a,b form a outline shape in the device 10 that conforms to a typical inferior angle of a pelvis in a patient and which follows the anatomical structure of the pubic rami.

The device 10 may be constructed from two separate pieces of plastic to form the base and top portions 11/12. The base portion is generally flat and acts as a base for the device and contacts directly against a patient. Some minor ribbing features (not shown) may be formed into the underside or lower surface 14 of base portion 11 to strengthen and provide it with additional rigidity. Horizontal ridges 13a,b are thermally formed into upper or top portion 12 that results in the recess 15 which is shaped to receive and capture a lower portion of a pneumatic tourniquet bladder applied over the device 10. While the device 10 is described with upper and lower portions 11/12 fused with grommets, it will be understood that these portions may be fixed together through adhesives or with heat welding, or any other suitable method to ensure sufficient bonding and resilience such that upper and lower portions are fixed in orientation and shape. Recess 15 presently is not fixed against the upper surface of base portion 11 because due to the resiliency of the upper portion plastic it is not necessary, and under tension the recess may simply rest against the upper surface of the base portion if deformed under pressure. However, the inventor anticipates that fusing of the recess undersurface into the upper surface of base portion 11 may be utilized to further increase the overall resiliency of the device 10.

The preferred dimensions of the device are 4 inches along edges 32a,b, 6 inches spanning leading edge 21 and trailing edge 22, and 7 inches along trailing edge 22. The distance between ridges 13a,b is approximately 3 inches, forming a slope of approximately 45 degrees down each ridge to the recess 15 and to leading and trailing edges 21/22 at the juncture of the base 11 and top 12 portions. The above indicated shape and size of the invention allows for maximum overlay of critical organs in the abdomen, and also to provide a practical and packable device for a medical field kit. The overall width of the device is also sized so that the recess 15 matches the maximum length of the lower end 126 of the bladder 20 when the two are engaged together.

While the actual ridge heights 13a,b are not critical, a ridge height of at least 1.5 inches is preferred to avoid rocking of the bladder 20 during inflation, and additional ridge height beyond 1.5 inches actually increases stability during the engagement of the bladder 20 on the device 10.

Figure 2:
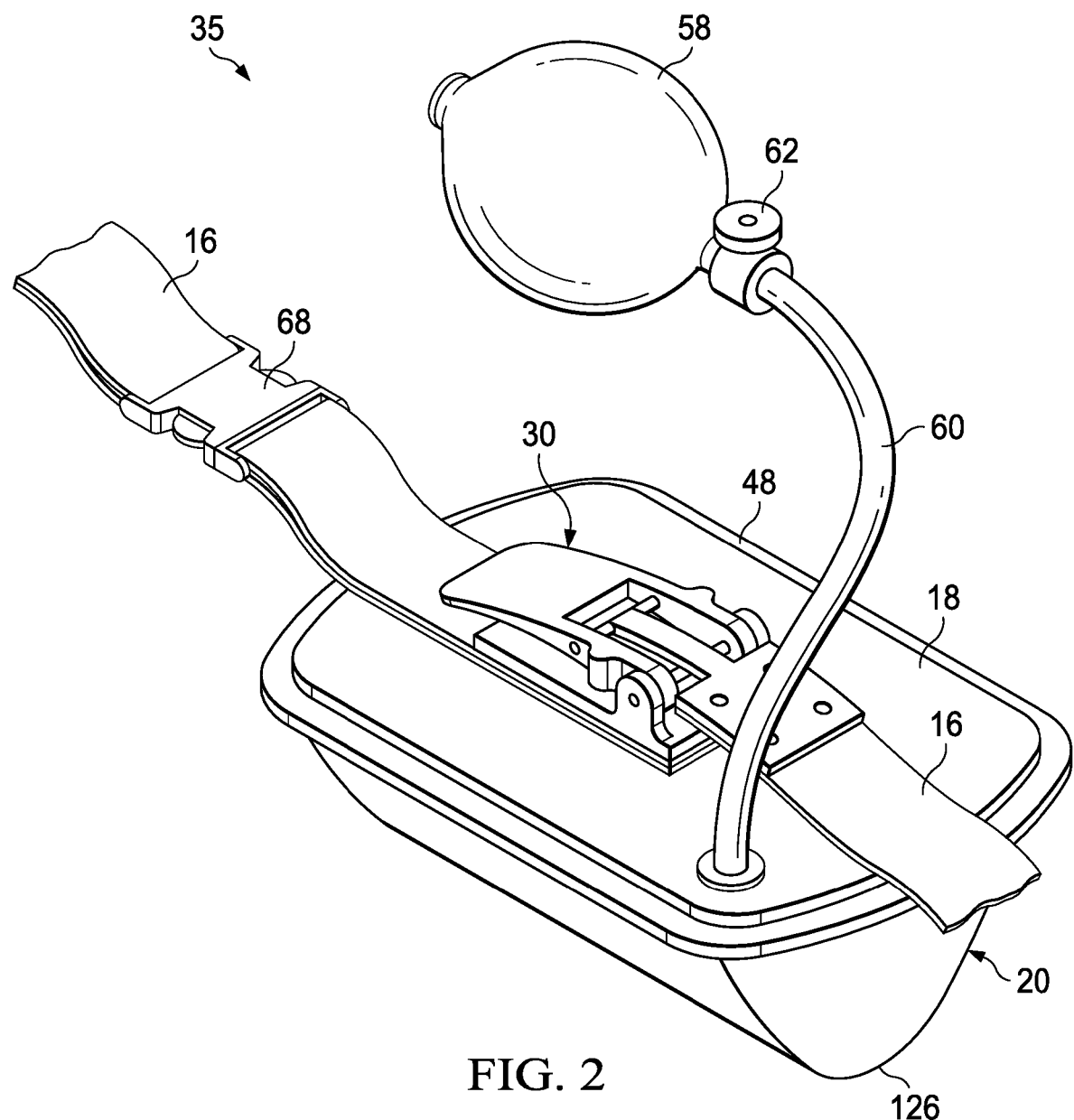
FIG. 2 is a perspective view of a compatible pneumatic tourniquet that may be used with the invention.

FIG. 2 provides a copy of FIG. 6 of U.S. Pat. No. 9,149,280B2 and shows a typical pneumatic tourniquet having essential functioning elements, which are described above in the Background of the Invention. The numerals of that FIG. 6 in U.S. Pat. No. 9,149,280B2 are replicated for this disclosure to facilitate discussion.

Figure 3:
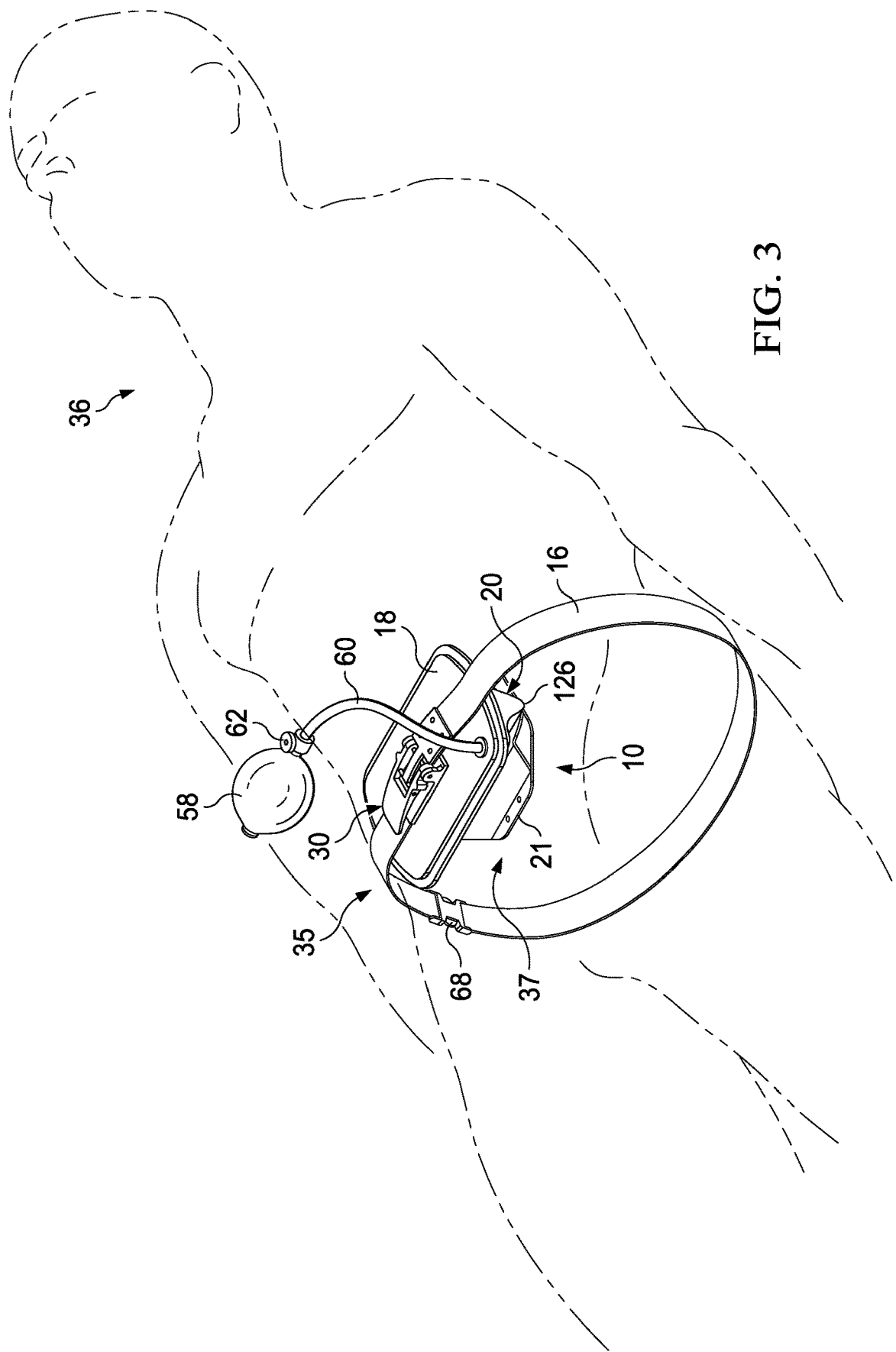
FIG. 3 is a perspective view of the compression device having an inflatable tourniquet apparatus positioned above the compression device and positioned for receiving the lower edge of a partially inflated bladder into a recess on the central top area of the compression device.

FIG. 3 shows the pneumatic tourniquet of FIG. 6 of U.S. Pat. No. 9,149,280B2 positioned over a patient with the compression device 10 in place underneath the pneumatic tourniquet with the bladder in a partially inflated state. As noted in that patent, FIG. 3 of U.S. Pat. No. 9,149,280B2 shows a typical pneumatic tourniquet with the hand pump bulb 58 replaced with a CO2 cartridge 28 for inflation. FIGS. 1A-2C of U.S. Pat. No. 9,149,280B2 show the typical positioning of the pneumatic tourniquet on a patient. FIGS. 1A-2C of U.S. Pat. No. 9,149,280B2 and the disclosure spanning Col. 3, line 60 through Col. 4, line 43 of U.S. Pat.

No. 9,149,280B2 are hereby incorporated by reference. Further discussion regarding the operation and functioning of the pneumatic tourniquet in U.S. Pat. No. 9,149,280B2 will be restricted to structures and processes intersecting with the compression device 10 since such disclosures are already fully developed in U.S. Pat. Nos. 8,834,517B2 and 9,149,280B2.

Referring to FIG. 3, the pneumatic tourniquet 35 is arranged over the lower abdomen 37 of a patient 36 to apply localized pressure over the pelvic region with the compression device 10 positioned under the bladder 20. The pneumatic tourniquet 35 includes an adjustable waist strap 16 for securing the pneumatic tourniquet and the compression device 10 on the pelvic area of the patient 36. The rigid base plate 18 is carried on waist strap 16 and supports the bladder against the compression device 10, and the directed air bladder 20 is carried on the bottom side of base plate 18. The bladder 20 is shown in a deflated condition and may be generally collapsed against base plate 18 until properly positioned against the compression device 10. With partial inflation of the bladder 20, the narrow lower end 126 of the bladder 20 extends and is arranged to be inserted into device recess 15 and held in place as the bladder further expands. As bladder 20 is expanded to extend outwardly from the bottom side of base plate 18 it exerts pressure on the compression device 10 against the patient 36 compressing the groin area 37. The air source used to inflate the bladder 20 may be a CO2 gas cartridge or a bulb pump 58 as shown. The pneumatic tourniquet 35 may also include a compression latch 30 affixed to base plate 18 and operatively associated with waist strap 16 for tightening waist strap 16 around the lower abdomen 37. Preferably, strap 16 also includes a quick connect buckle 68 to facilitate arrangement of the pneumatic tourniquet 35 around the patient 36 that then allows for the compression latch 30 to be closed.

Figure 4:
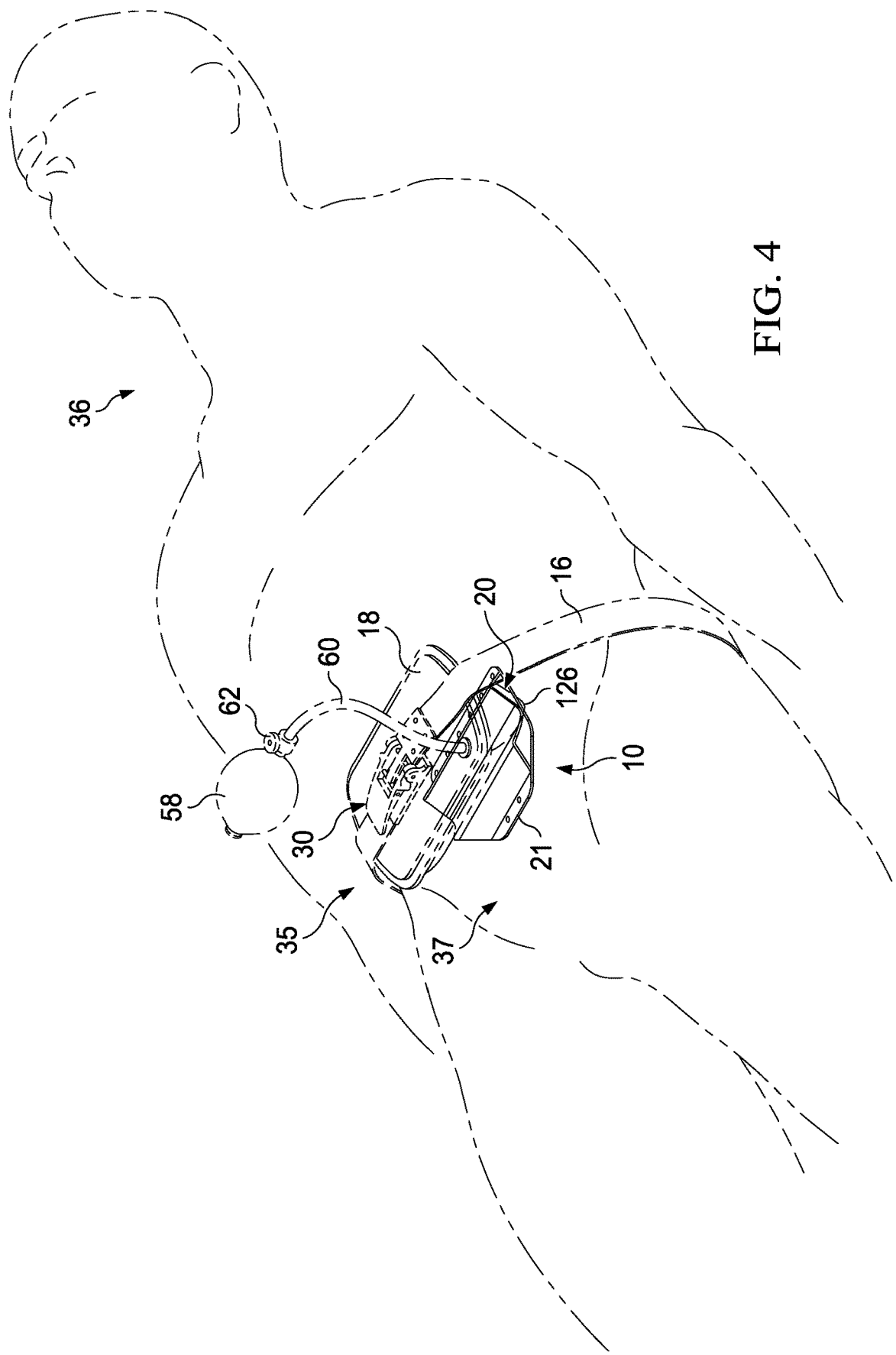
FIG. 4 is a perspective view of the compression device fully engaged on a patient applying pressure with the compatible pneumatic tourniquet shown in phantom; and, FIG. 5 is a flow diagram showing the steps for usage of the compression device with a compatible pneumatic tourniquet on a patient.

Referring to now to FIG. 4, it may be seen a patient 36 with a compression device 10 positioned on the abdomen prior to arranging the pneumatic tourniquet 35 over the patient 36. As shown, the tapered end of the compression device 10 is oriented upwards towards a patient's head, but below the ribs of the patient, for compression of the upper-mid abdomen. For usage in lower abdomen and pelvic regions, the device 10 is rotated 180 degrees so that the tapered end is oriented downwards and positioned over the human pelvis with the ridges positioned away from the patient and the lower surface of the base 11 positioned toward and in contact with the patient 36. The pneumatic tourniquet is placed over the compression device and secured around the patient's hips. Slack is removed from the belt of the pneumatic tourniquet and the compression device tightened against with patient at the appropriate site on the pelvis. The recess 15 is shaped to receive the bladder lower end 126 as described above such that upon inflation of the bladder and focused engagement of the base 11 against the patient, the compression device 10 and the pneumatic tourniquet 35 are secured and fixed to the patient in a static state, and the pelvic region is compressed as more air pressure is exerted into the bladder 20. While not always necessary, a windlass (see for example, element 85 of FIG. 8 of U.S. Pat. No. 9,149,280B2) on the pneumatic tourniquet 35 may be utilized to further tighten the pneumatic tourniquet 35 and compression device 10 against the patient, but in either case the bladder 20 is inflated to at least 250 mm Hg pressure. The compression device 10 distributes the pneumatic tourniquet 35 pressure from bladder 20 in a uniform manner and over a larger area than the tapered bladder 20, thereby increasing the intra-pelvic compartment pressure from the exterior pressure application. The combination of the pneumatic tourniquet 35 and compression device 10 also provides pressure in a wedge shaped distribution which is effective at blocking blood flow through arterial vessels to the pelvic area. The device uses the flat underside to achieve an equally distributed pressure over the pelvic region, and is effective to alter the generally wedge pressure distribution of the pneumatic tourniquet to that of a flat distribution over the pelvic region.

The compression device may be especially helpful in post-partum hemorrhaging emergencies where sophisticated surgical facilities are unavailable.

Figure 5:
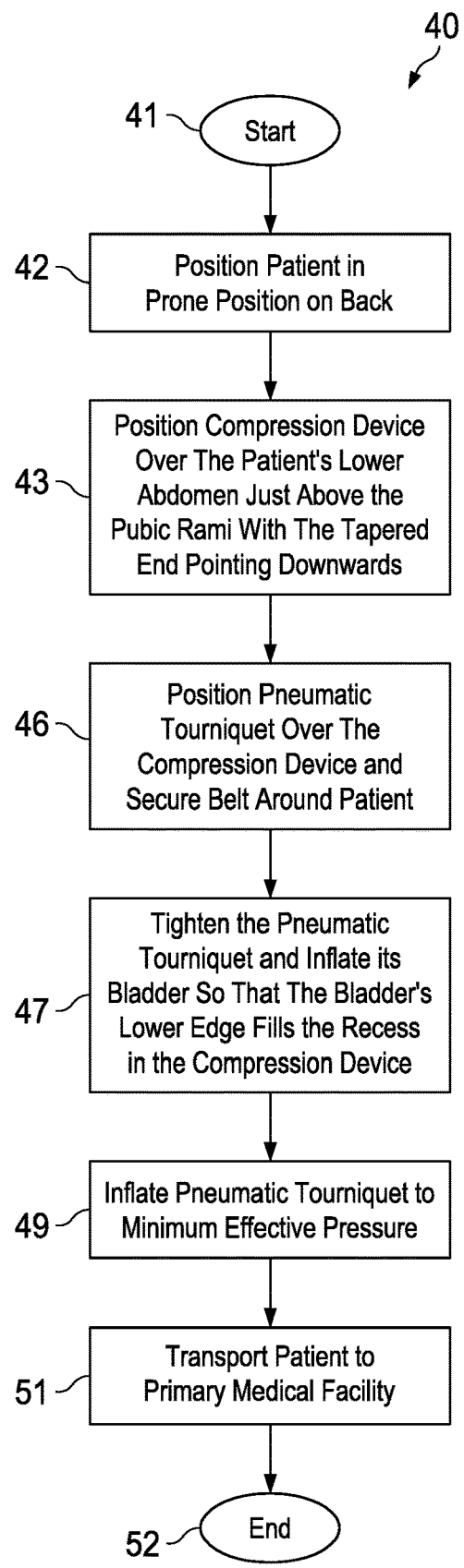

Referring finally to FIG. 5, it may be seen the preferred steps 40 in utilizing the compression device 10 by a field medic or emergency responder. A patient should be arranged into a prone position on their back 42. The compression device 10 is positioned 43 on the patient with the flat lower surface 11 in contact with the patient's lower abdomen or groin just above the pubic rami, with the tapered end pointing downwards towards the pubic rami. The pneumatic tourniquet 35 is then arranged 46 over and around the patient 36 in a manner that allows for the bladder 20 to be in proximity to the compression device 10. The pneumatic tourniquet 35 is tightened around the patient 36 and the bladder 20 inflated 47 so that bladder's lower edge 126 fills the recess 15 in the compression device 10. It is critical that the tapered end of the compression device 10 be oriented downwards toward and just above the pubic rami so that a substantial area of the inguinal region is affected. As may be understood, the straps 16 and buckles and latches 68/30 would be adjusted so that the pneumatic tourniquet 35 is fitted correctly around patient 36 and over the compression device 10. As may also be understood, steps 43, 46, and 47 may be varied such that the compression device 10 may be positioned on the inguinal region of the patient simultaneously with or after the pneumatic tourniquet 35 is fitted over the patient, depending upon practice and training of each medical practitioner to accommodate different patient sizes and shapes, and to adjust to field conditions in which the patient is situated. The bladder 20 of the pneumatic tourniquet 35 is inflated further 49 to a minimum effective pressure of 250 mm Hg exerted against the inguinal region and lower abdomen, but not more than 300 mm Hg pressure. In order to ensure that 300 mm Hg are not exceeded, a medical practitioner may use a manometer connected to pressure tube 60 of the pneumatic tourniquet to monitor the pressure and cease pumping air into the bladder 20, or release air from the relief valve 62, or alternatively the pressure relief valve 62 may be preset to release pressure automatically when the tube 60 pressure exceeds 300 mm Hg. Additional pressure feedback may be provided by the pressure relief valve 62 or another type of pressure adjustment mechanism, as may be understood.

The inventor has observed that an external minimum pressure from bladder 20 results in a minimum inter-pelvic compartment pressure of 40 mm Hg. Hence, a minimum external pressure of 250 mm Hg should be applied to the patient and held for at least 20 minutes to arrest internal bleeding. Such inter-compartmental pressure will not permanently damage the targeted area or surrounding tissues. After that minimum period of time, cessation of blood flow from organs, such as a uterus, will abate considerably and quite often will stop entirely. Also, after that minimum timer period, the pneumatic tourniquet pressure may be reduced below the critical external pressure to allow for comfort of the patient or for further field examinations. Once the compression device 10 has been pressurized by the pneumatic tourniquet 35 (i.e. after step 49) the patient may be transported 51 to a primary medical facility for further treatment.

While I have shown my invention in one form, it will be obvious to those skilled in the art that it is not so limited but is susceptible of various changes and modifications without departing from the spirit thereof. For example, while use of the invention with a pneumatic tourniquet has been provided as an example, the inventor anticipates that a mechanical substitute may be devised that will allow for the controlled application of pressure to the upper surface of the device 10 for similar satisfactory inter-abdominal pressure results. In addition, various types of textured surfaces such as a non-skid tape or similar material may be applied onto the upper 12 and lower 11 portion surfaces to enhance engagement of the pneumatic tourniquet 35 with the compression device 10.

Having set forth the nature of the invention, what is claimed is:

1. In combination with a pneumatic tourniquet having an inflatable bladder with a lower end, an air source for inflating said inflatable bladder, means for securing said pneumatic tourniquet over a pubic rami area of a pelvis of a patient, said pubic rami and said pelvis forming in theft anatomical structure an inferior angle at their intersection thereof, and a pressure control device for controlling pressure in said inflatable bladder, a compression device for arresting hemorrhage in an inguinal area of the patient, comprising:
   a. a base portion in contact with the inguinal area of said patient, said base portion including a substantially flat underside;
   b. a corrugated upper portion supported by said base portion;
   c. wherein said corrugated upper portion includes a centrally positioned recess adapted to receive said lower end of said inflatable bladder, and wherein pressure exerted by said lower end on said compression device is transferred to said patient;
   d. wherein said base portion and said corrugated upper portion are affixed to one another to form a unified whole; and,
   e. wherein said compression device includes a tapered end shaped to match the inferior angle formed by the anatomical structure of the pubic rami and the pelvis.

2. The compression device as recited in claim 1, further including a pair of ridges spanning across said compression device such that said pair of ridges define said recess.

3. The compression device as recited in claim 2, wherein said pair of ridges further define a pair of interior facing slopes adapted to match an exterior surface of said lower end of said inflatable bladder to form a cooperative fit when joined together.

4. The compression device as recited in claim 3, wherein said base portion and said corrugated upper portion define a hollow space between them.

5. The compression device as recited in claim 4, wherein said base portion and said upper portions include fused margins on opposite sides of said compression device.

6. The compression device as recited in claim 1, wherein said recess includes slopping sides adapted to match an exterior surface of said lower end of said inflatable bladder to form a cooperative fit when joined together.

7. A compression device for controlling internal bleeding in a human inguinal area, said inguinal area supporting a pubic rami and said inguinal area being supported by a pelvis of a human, wherein an anatomical intersection of said pubic rami and said pelvis forms an inferior angle, comprising:
   a. a substantially rectangular member having a tapered end and a recess centrally disposed within said rectangular member, said tapered end shaped to match the inferior angle formed by the anatomical intersection of said pubic rami and said pelvis;
   b. a pair of parallel ridges spanning across said rectangular member, wherein said pair of parallel ridges define said central recess; and,
   c. wherein said central recess is adapted to receive a compressive member of an external tourniquet designed to apply external pressure to a human body to stop bleeding, wherein said compression device distributes force exerted by said compressive member uniformly over said inguinal area.

8. The compression device as recited in claim 7, wherein said rectangular member and said pair of parallel ridges define a hollow space within said compression device.

9. The compression device as recited in claim 8, wherein said rectangular member includes a pair of fused margins on opposite sides thereof.

10. A compression device for controlling inguinal hemorrhaging in a human by uniformly distributing pressure exerted by a pneumatic tourniquet over an inguinal area of said human and including exerting pressure over a pubic rami area of a pelvis of said human, wherein said pubic rami and said pelvis form an inferior angle at theft intersection due to the anatomical structure of said inguinal area, said pneumatic tourniquet including an inflatable bladder with a lower end oriented toward said inguinal area, an air source for inflating said inflatable bladder, a strap for fitting and securing said pneumatic tourniquet over a patient for applying pressure, and a pressure control device for controlling pressure in said inflatable bladder, said compression device comprising:
   a. a substantially flat member having a tapered end and a recess centrally disposed within said substantially flat member;
   b. a pair of parallel ridges spanning across said substantially flat member, wherein said pair of parallel ridges define said central recess;
   c. wherein said compression device is adapted to be positioned between said lower end of said inflatable bladder and the inguinal area of said human, and wherein said compression device is adapted to be positioned with said tapered end positioned just above the pubic rami of said inguinal area, and wherein said tapered end matches the inferior angle formed by the anatomical structure of the public rami and said pelvis; and
   d. wherein upon pressurizing said inflatable bladder to at least 250 mm Hg pressure said compression device responsively distributes pressure of said inflatable bladder over said inguinal area such that inter-compartmental pressure of said inguinal area increases to at least 40 mm Hg of internal pressure thereby stopping internal hemorrhaging.

11. In combination with a pneumatic tourniquet having an inflatable bladder with a lower end, an air source for inflating said inflatable bladder, means for securing said pneumatic tourniquet over a patient, and a pressure control device for controlling pressure in said inflatable bladder, and in combination with a compression device having a base portion including a substantially flat underside, a corrugated upper portion supported by said base portion, wherein said base portion and said corrugated upper portion are fused to form a unified device, and wherein said unified device has a tapered end shaped to match an inferior angle formed by an anatomical structure of a pubic rami and a pelvis of a human being, and a recess disposed within the center of said compression device, a method for arresting inguinal hemorrhage in a human patient, comprising the steps of:

a. positioning said human patient on their back in a prone position;
b. positioning said compression device over an inguinal area of said human patient just above the pubic rami of said inguinal area with said tapered end pointing downwards to match the inferior angle formed by the anatomical structure of the pubic rami and the pelvis of said human patient;
c. positioning said pneumatic tourniquet over said compression device and securing said pneumatic tourniquet around said human patient;
d. tightening said pneumatic tourniquet around said human patient and inflating said inflatable bladder so that said lower end of said inflatable bladder fills said recess in said compression device;
e. inflating said pneumatic tourniquet to a minimum effective pressure; and
f. transporting said human patient to a primary medical facility.

12. A method as recited in claim 11, wherein said minimum effective pressure is at least 250 mm Hg pressure.

13. A method as recited in claim 12, further comprising the step of controlling pressure in said inflatable bladder such that pressure within said inflatable bladder never exceeds 300 mm Hg pressure.

14. A method as recited in claim 13, wherein said step of inflating said inflatable bladder causes an inter-compartmental pressure of said inguinal area to be raised by at least 40 mm Hg pressure.

15. A method as recited in claim 14, wherein said minimum effective pressure is maintained for at least 20 minutes.

16. A method as recited in claim 11, wherein said step of inflating said inflatable bladder causes an inter-compartmental pressure of said inguinal area to be raised by at least 40 mm Hg pressure.

17. A method as recited in claim 16, wherein said minimum effective pressure is maintained for at least 20 minutes.

18. A method for controlling hemorrhaging in an inguinal area of a pelvis of a human patient, wherein said inguinal area supports a pubic rami in said pelvis, and wherein said pubic rami and said pelvis form an inferior angle at their intersection thereof, said method comprising the steps of:

a. positioning said human patient on theft back in a prone position;
b. positioning a compression device having a substantially flat under surface over the inguinal area of said human patient just above the pubic ram of said inguinal area, said compression device including a corrugated upper portion defining a centrally positioned recess spanning across said compression device, said compression device further including a tapered end shaped to match the inferior angle formed by the anatomical structure of said pubic rami in said pelvis, and wherein said step of positioning said compression device includes positioning said tapered end to be aligned with said inferior angle formed by the anatomical structure of said pubic rami and said pelvis;
c. positioning a pneumatic tourniquet over said compression device and securing said pneumatic tourniquet around said human patient;
d. tightening said pneumatic tourniquet around said human patient with straps and inflating a bladder on said compression device such that the lower end of said bladder fills said centrally disposed recess within said compression device;
e. further inflating said bladder such that said compression device exerts pressure against said inguinal area thereby decreasing said hemorrhaging.

19. A method as recited in claim 18, wherein said step of further inflating said bladder causes an inter-compartmental pressure of said inguinal area be raised by at least 40 mm Hg pressure.

20. A method as recited in claim 19, wherein said step of further inflating said bladder causes said bladder to have a minimum internal pressure of 250 mm Hg and said inter-compartmental pressure of at least 40 mm Hg in said inguinal area is maintained for at least 20 minutes.

* * * * *